United States Patent [19]

Hill

[11] 4,165,380

[45] Aug. 21, 1979

[54] BIS(SULFIDE)GOLD(1+) SALTS

[75] Inventor: David T. Hill, North Wales, Pa.

[73] Assignee: SmithKline Corporation, Philadelphia, Pa.

[21] Appl. No.: 912,137

[22] Filed: Jun. 2, 1978

Related U.S. Application Data

[62] Division of Ser. No. 772,034, Feb. 25, 1977, Pat. No. 4,112,113.

[51] Int. Cl.² .................... A61K 31/28; C07F 1/12
[52] U.S. Cl. ................................. 424/290; 260/430
[58] Field of Search .................... 260/430; 424/290

[56] References Cited

U.S. PATENT DOCUMENTS

| | | | |
|---|---|---|---|
| 3,438,748 | 4/1969 | Tavernier et al. | 260/430 X |
| 3,635,945 | 1/1972 | Nemeth et al. | 260/430 X |
| 3,661,959 | 5/1972 | Vaughan | 260/430 |
| 3,676,554 | 7/1972 | McGusty et al. | 260/430 X |
| 3,718,679 | 2/1973 | McGusty et al. | 260/430 |
| 3,718,680 | 2/1973 | McGusty et al. | 260/430 |
| 3,842,107 | 10/1974 | Sutton et al. | 260/430 |
| 3,842,108 | 10/1974 | Sutton et al. | 260/430 |
| 3,883,546 | 5/1975 | Sutton et al. | 260/430 X |

OTHER PUBLICATIONS

Roulet et al., Helv. Chim. Acta 56(7), pp. 2405–2418, (1973).
Brain et al., J. Chem. Soc., pp. 3686–3694, (1952).

*Primary Examiner*—Helen M. S. Sneed
*Attorney, Agent, or Firm*—Joan S. Keps; Richard D. Foggio; William H. Edgerton

[57] ABSTRACT

The compounds are bis(sulfide)gold(1+) salts which have antiarthritic activity.

4 Claims, No Drawings

BIS(SULFIDE)GOLD(1+) SALTS

This is a division of application Ser. No. 772,034 filed Feb. 25, 1977, now U.S. Pat. No. 4,112,113.

This invention relates to new bis(sulfide)gold(1+) salts. These compounds have antiarthritic activity and, in particular, are of use in the treatment of rheumatoid arthritis.

The compounds of this invention are represented by the following formula:

FORMULA I

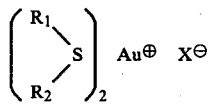

in which $R_1$ and $R_2$ and 2-hydroxyethyl or taken together with the sulfur atom to which they are attached form a tetrahydrothienyl or tetrahydrothiapyranyl ring and X is a weekly nucleophilic anion.

A particular compound of this invention is represented by Formula I in which $R_1$ and $R_2$ taken together with the sulfur atom to which they are attached form a tetrahydrothienyl ring.

The anion X in Formula I is a weakly nucleophilic anion such as, for example, perchlorate ($ClO_4$), iodate ($IO_4$), tetrafluoroborate ($BF_4$) and hexafluorophosphate ($PF_6$).

The compounds of this invention are prepared by the following procedure:

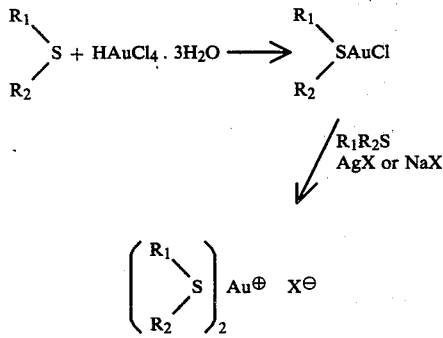

The terms $R_1$, $R_2$ and X are as defined above.

According to the above procedure, a sulfide, $R_1R_2S$, is reacted with gold acid chloride trihydrate to give the chloro(sulfide)gold compound $R_1R_2SAuCl$. This reaction is carried out in a suitable solvent, such as aqueous ethanol, conveniently at room temperature. The chloro(sulfide)gold compound is reacted with a silver salt AgX or a sodium salt NaX and a sulfide $R_1R_2S$. This reaction is carried out in a solvent, such as acetone, at room temperature. The products are the bis(sulfide)gold(1+) salts of this invention.

The compounds of this invention are useful in treatment of arthritis. This activity is demonstrated by the following test procedures.

Inhibition of adjuvant induced polyarthritis in rats, as measured by reduction of rat paw edema, is produced by compounds of this invention at daily oral doses of about 20 mg./kg. (calculated on gold content). In this test procedure, adjuvant arthritis in rats is produced by a single intradermal injection of 0.75 mg. of *Mycobacterium butyricum* suspended in white paraffin oil into the left hindpaw footpad. The injected paw becomes inflamed (increased volume) and reaches maximal size within three to five days (primary lesion). The animals exhibit a decrease in body weight gain during the initial period. The adjuvant arthritis (secondary lesion) occurs after approximately ten days and is characterized by inflammation of the non-injected right hind leg, decrease in body weight, and further increase in the volume of the injected left hind leg. Test compounds are administered daily, beginning on the day of the adjuvant injection, for 17 days thereafter, exclusive of days 4, 5, 11 and 12. Antiarthritic activity is shown by the ability to inhibit the development of either primary or secondary lesions of adjuvant arthritis.

The compounds of this invention are administered in conventional dosage forms prepared by combining a compound of Formula I in an amount sufficient to produce antiarthritic activity with standard pharmaceutical carriers according to conventional procedures. These procedures may involve mixing, granulating and compressing or dissolving the ingredients as appropriate to the desired preparation. The resulting pharmaceutical compositions are also objects of this invention. Oral dosage forms are preferred.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampule or nonaqueous liquid suspension.

Preferably, each dosage unit will contain the active ingredient in an amount of from about 1 mg. to about 10 mg.

The method of producing antiarthritic activity by administering internally to an animal a compound of Formula I is also an object of this invention. The compounds of Formula I are administered in an amount sufficient to produce antiarthritic activity. The route of administration may be orally or parenterally, preferably orally. Advantageously, doses will be administered 1 or 2 times a day, with the daily dosage regimen being preferably from about 1 mg. to about 12 mg. When the method is carried out as described above, antiarthritic activity is produced.

One skilled in the art will recognize that in determining the amounts of the active ingredient in the claimed compositions and used in the claimed methods, the activity of the chemical ingredient as well as the size of the host animal must be considered.

The following examples are not limiting but are illustrative of the invention.

EXAMPLE 1

A solution of 4.0 g. (0.045 mole) of tetrahydrothiophene in 15 ml. of ethanol was added dropwise to a solution of 5.0 g. (0.013 mole) of gold acid chloride trihydrate in 15 ml. of distilled water maintained at room temperature. After stirring 15 minutes, the precipitate was removed by filtration, washed with water, then ethanol and finally ether. Crystallization from ethanol gave chloro(tetrahydrothienyl)gold(I), m.p. 148°–150° C.

A solution of 0.087 g. (0.004 mole) of silver perchlorate in 15 ml. of acetone was added dropwise to a mixture of 1.32 g. (0.004 mole) of chloro(tetrahydrothienyl)gold(I) and 2 ml. of tetrahydrothiophene in 30 ml. of acetone and 5 ml. of methylene chloride. After stirring for 30 minutes, the precipitate was removed by filtration and the solvent removed at reduced pressure to give an oil. The oil was washed with ether and the ether layer decanted. The resultant oil was dissolved in methylene chloride, filtered and the solvent removed at reduced pressure to give bis(tetrahydrothienyl)gold(1+)perchlorate, m.p. 114°–120° C.

EXAMPLE 2

By the procedure of Example 1, tetrahydrothiapyran is reacted with gold acid chloride trihydrate to give chloro(tetrahydrothiapyranyl)gold(I).

Adding an acetone solution of silver perchlorate to a mixture of chloro(tetrahydrothiapyranyl)gold(I) and tetrahydrothiapyran in acetone and methylene chloride, stirring the resulting mixture for 30 minutes, then working up by the procedure of Example 1 gives bis(tetrahydrothiapyranyl)gold(1+)perchlorate.

Using silver iodate in the above procedure in place of silver perchlorate gives bis(tetrahydrothiapyranyl)gold(1+)iodate.

EXAMPLE 3

Using silver tetrafluoroborate in place of silver perchlorate in the procedure of Example 1, the product is bis(tetrahydrothienyl)gold(1+)tetrafluoroborate.

Similarly, using silver hexafluorophosphate, the product is bis(tetrahydrothienyl)gold(1+)hexafluorophosphate.

EXAMPLE 4

6.2 Grams (0.051 mole) of di(2-hydroxyethyl)sulfide was added to 10 g. (0.025 mole) of gold acid chloride trihydrate in 100 ml. of ethanol at 25° C. After one hour, the solvent was removed at reduced pressure. The resultant oil was dissolved in acetone and chromatographed over silica gel (acetone) to give chloro[di(2-hydroxyethyl)sulfide]gold(I) as an orange oil.

A solution of 2.28 g. (0.011 mole) of silver perchlorate in 70 ml. of acetone is added to a solution of 4.0 g. (0.011 mole) of chloro[di(2-hydroxyethyl)sulfide]gold(I) and 5 ml. of di(2-hydroxyethyl)sulfide in 80 ml. of acetone. After stirring for 30 minutes at room temperature, the mixture is filtered and the solvent removed at reduced pressure. The residue is dissolved in methylene chloride, filtered and the solvent removed at reduced pressure to give bis[di(2-hydroxyethyl)sulfide]gold(1+)perchlorate.

EXAMPLE 5

| Ingredients | Amounts |
|---|---|
| bis(tetrahydrothienyl)gold(1+) perchlorate | 5 mg. |
| magnesium stearate | 5 mg. |
| lactose | 200 mg. |

The above ingredients are screened, mixed and filled into a hard gelatin capsule.

The capsules are administered orally to subjects in need of antiarthritic treatment in amounts within the daily dose range given hereabove.

Similarly, the other gold compounds of Formula I may be formulated into capsules by the procedure of Example 5.

Other pharmaceutical compositions such as tablets containing a compound of Formula I as the active ingredient are formulated by standard procedures.

What is claimed is:

1. A compound of the formula:

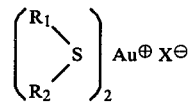

in which $R_1$ and $R_2$ are 2-hydroxyethyl and X is a weakly nucleophilic anion.

2. A compound of claim 1 in which X is perchlorate, iodate, tetrafluoroborate or hexafluorophosphate.

3. A pharmaceutical composition having antiarthritic activity, in dosage unit form, comprising a pharmaceutical carrier and in an amount sufficient to produce antiarthritic activity a compound of claim 1.

4. A method of producing antiarthritic activity which comprises administering internally to an animal in an amount sufficient to produce antiarthritic activity a compound of claim 1.

* * * * *